(12) United States Patent
Kim et al.

(10) Patent No.: US 7,855,188 B2
(45) Date of Patent: Dec. 21, 2010

(54) QUARTERNIZED AMINO GLUCOSAMINE COMPOUND FOR EXERTING ANTICANCER EFFECT

(75) Inventors: Moon-Moo Kim, Busan (KR); Se-Kwon Kim, Busan (KR); Eresha Mendis, Busan (KR)

(73) Assignee: Pukyong National University Industry-Academic Cooperation Foundation, Busan (KR)

( * ) Notice: Subject to any disclaimer, the term of this patent is extended or adjusted under 35 U.S.C. 154(b) by 0 days.

(21) Appl. No.: 11/910,403

(22) PCT Filed: Sep. 14, 2006

(86) PCT No.: PCT/KR2006/003671

§ 371 (c)(1),
(2), (4) Date: Jan. 16, 2008

(87) PCT Pub. No.: WO2008/007825

PCT Pub. Date: Jan. 17, 2008

(65) Prior Publication Data

US 2009/0176978 A1 Jul. 9, 2009

(30) Foreign Application Priority Data

Jul. 10, 2006 (KR) .................... 10-2006-0064389

(51) Int. Cl.
*A61K 31/7008* (2006.01)
(52) U.S. Cl. .................................. 514/62; 536/55.2
(58) Field of Classification Search .................. None
See application file for complete search history.

(56) References Cited

FOREIGN PATENT DOCUMENTS

WO   WO-2004/080490 A2   9/2004

OTHER PUBLICATIONS

Huang, R. et al "Improvement of ACE inhibitory activity of chitooligosaccharides . . . " Bioorg. Med. Chem. (2005) vol. 13, pp. 3649-3655.*
Giraud, I. et al "Application to a cartilage targetting strategy . . . " Bioconj. Chem. (2000) vol. 11, pp. 212-218.*
McKenny et al. Journal of Biotechnology. 2000, 83 (1,2), p. 37-44.
McKenny et al. "Broadly protective vaccine for *Staphylococcus aureus* based on an in vivo-expressed antigen". Science, 1999, 284 (5419), p. 1523-1527.
Kadokawa et al. Macromolecular Rapid Communications, 1994, 15 (12), p. 971-978.
Dardoize et al. "4-Hydroxybutyric acid (and analogs) derivatives of D-glucosamine". Tetrahedron, 1989, 45 (24), p. 7783-7794.
McKenny et al. "Vaccine potential of poly-1-6 β-D-$N$-succinylglucosamine, an immunoprotective surface polysaccharide of *Staphylococcus aureus* and *Staphylococcus epidermidis*". Journal of Biotechnology, 2000, 83 (1,2), p. 37-44.
Kadokawa et al. "Regioselective polycondensation of $N$-carboxyalkanoyl-$_D$-glucosamine using the hexachlorotriphosphazene/pyridine system as a condensing agent". Macromolecular Rapid Communications, 1994, 15 (12), p. 971-978.

* cited by examiner

*Primary Examiner*—Leigh C Maier
(74) *Attorney, Agent, or Firm*—Birch, Stewart, Kolasch & Birch, LLP

(57) ABSTRACT

The present invention relates to the quaternized amino glucosamine, it can exert an anticancer effect via induction of apoptosis in a dose and time dependant manner through which an anticancer treatment effect can be increased.

3 Claims, 5 Drawing Sheets

[Figure 1]
[Figure 2]
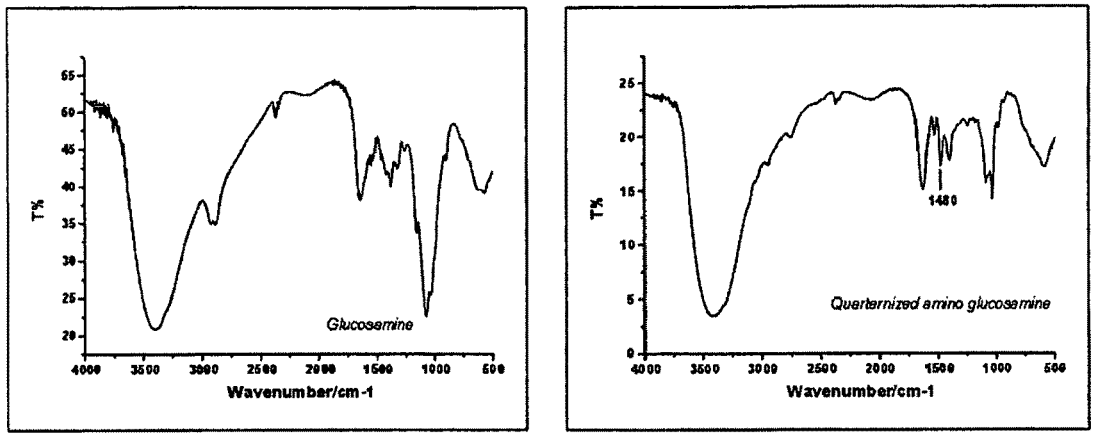
| Concentration (%) | Anticancer Effect (%) | | | | |
|---|---|---|---|---|---|
| | SW480 | A549 | B15F1 | HL60 | Hep3B |
| 0.01 | 92.69±2.56 | 48.38±0.72 | 58.84±1.56 | 98.69±2.34 | 88.28±1.06 |
| 0.005 | 89.87±2.03 | 25.80±1.40 | 42.88±1.73 | 93.77±2.16 | 68.12±1.36 |
| 0.001 | 42.14±0.96 | 23.47±0.54 | 35.79±1.46 | 62.36±1.24 | 23.00±0.86 |
| 0.0005 | 29.81±1.06 | 2.24±0.23 | 13.74±0.76 | 46.07±1.51 | 21.17±0.58 |

[Figure 3]
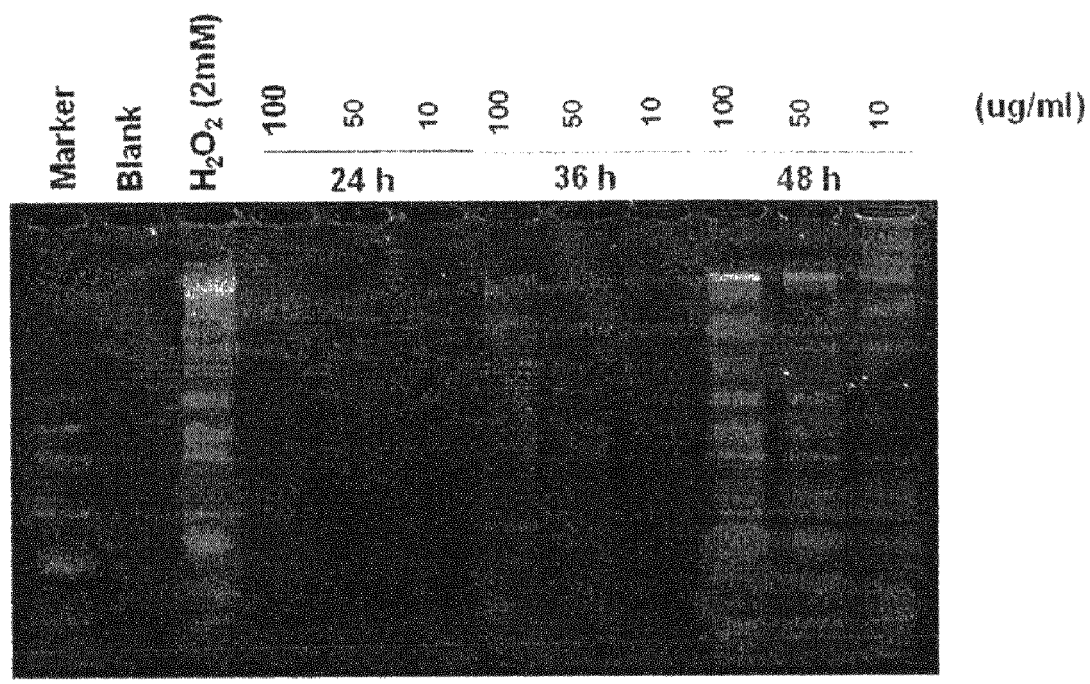

[Figure 4]
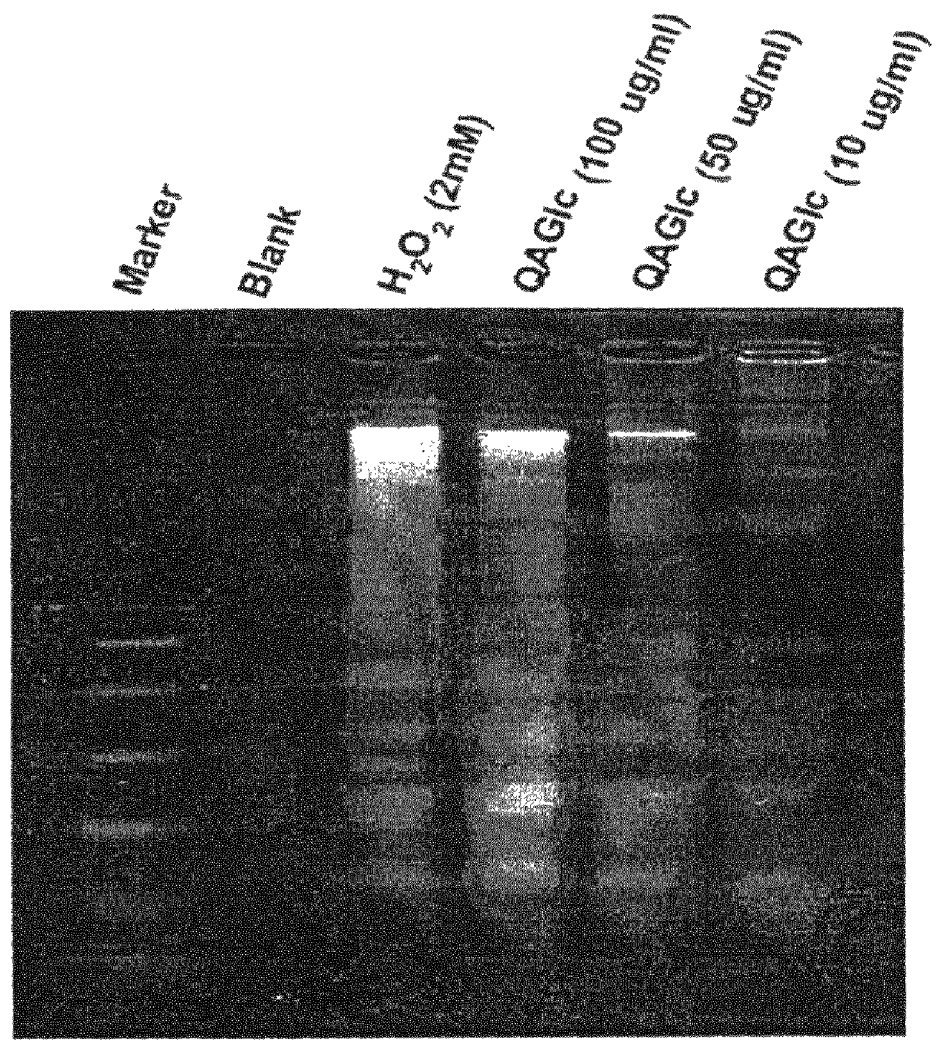
[Figure 5]
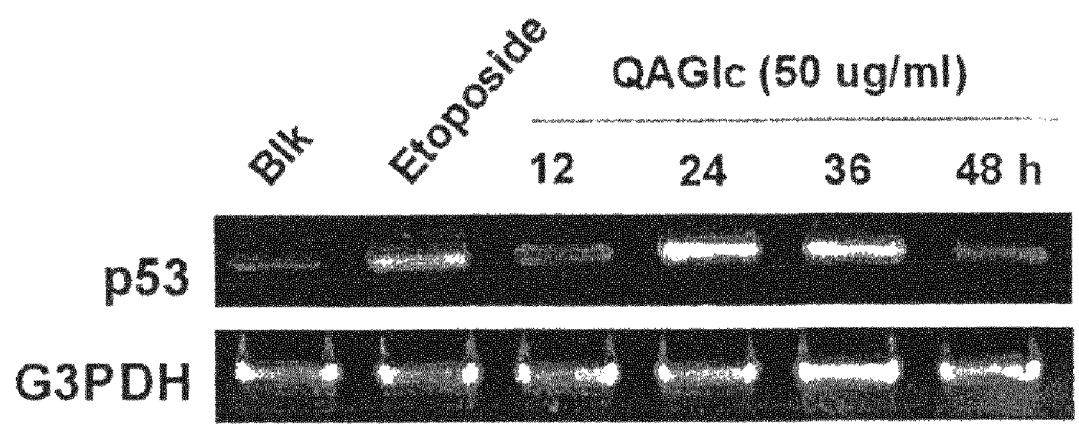

[Figure 6]
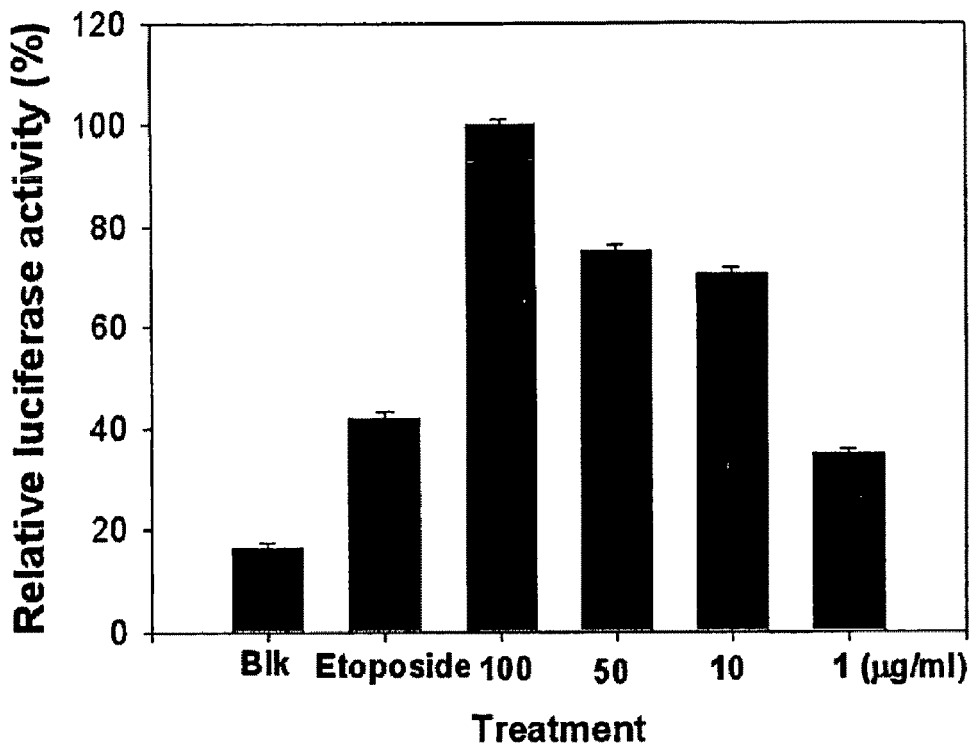
[Figure 7]
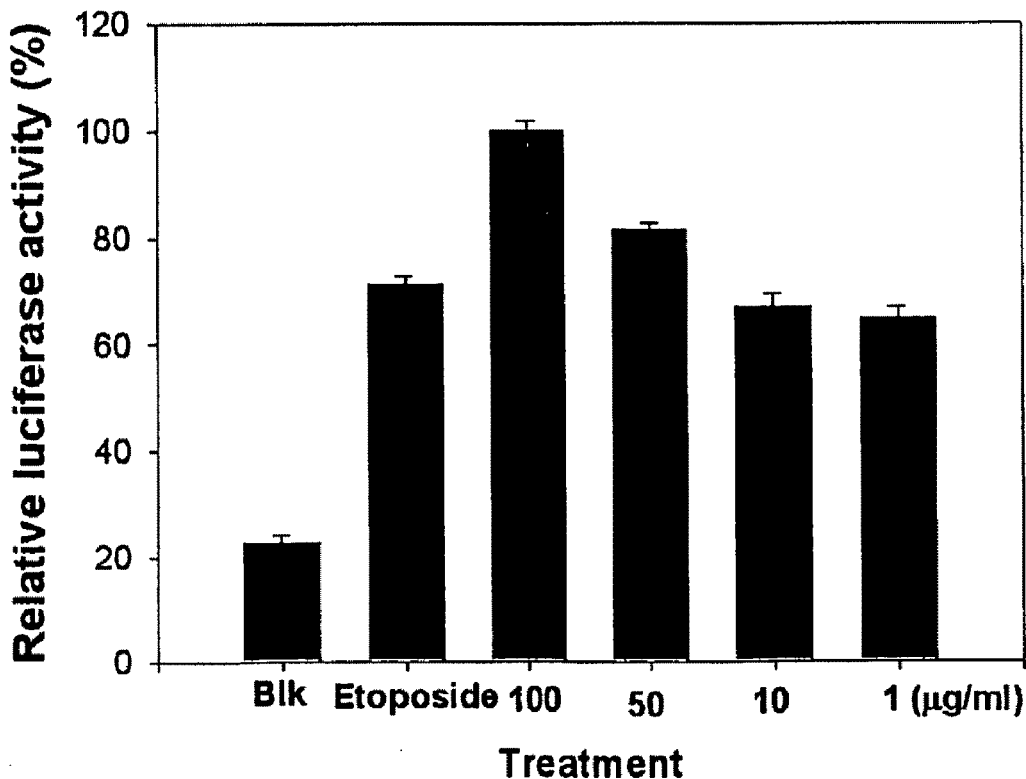

[Figure 8]
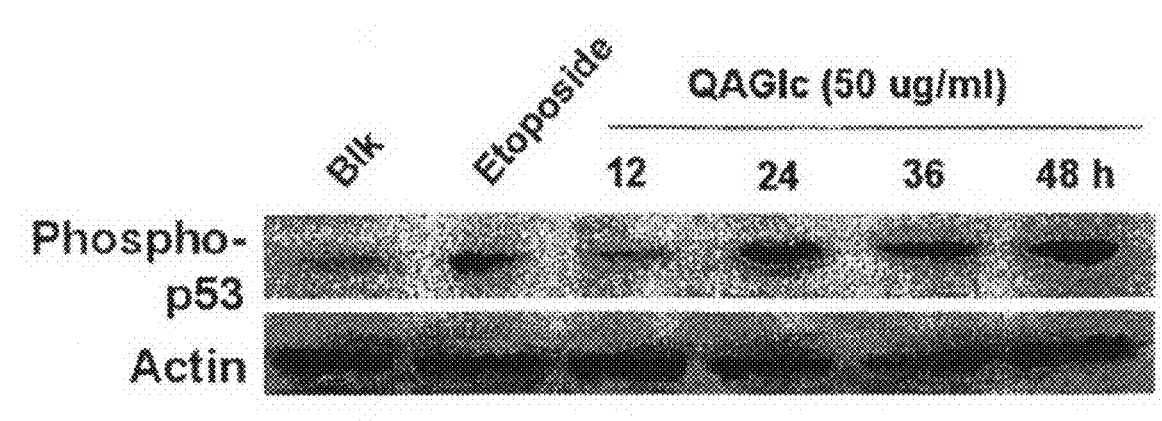

QUARTERNIZED AMINO GLUCOSAMINE COMPOUND FOR EXERTING ANTICANCER EFFECT

TECHNICAL FIELD

The present invention relates to a quaternized amino glucosamine (QAGlc) compound of formula 1 having anticancer effect, more specifically, to the quaternized amino glucosamine compound which can exert an anticancer effect via induction of apoptosis in a dose and time dependant manner through which an anticancer treatment effect can be increased.

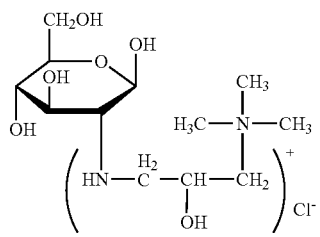

<Formula 1>

BACKGROUND ART

Apoptosis is the mechanism of cell death activated in mammalian cells following exposure to a wide variety of stimuli including anticancer agents. The chemotherapeutic agents that have been identified as being apoptosis-inducing include etoposide, dexamethasone, vincristine, cis-platinum, cyclophosphamide, paclitaxel, 5'-fluorodeoxyuridine, 5'-fluorouracil and adriamycin. The efficiency of the anticancer agents seems to be related to the intrinsic propensity of the tumor cells to respond to these agents by apoptosis. This indicates that apoptosis may be the primary mechanism in antineoplastic agents.

Apoptosis is an orchestrated series of events through which the cell precipitates its own death. The stages of apoptosis include cell shrinkage, chromatin condensation, nuclear segmentation and internucleosomal fragmentation of DNA, resulting in the generation of apoptotic bodies. Induction of apoptosis has been used as an index to screen for new anticancer substances and to study the anticancer mechanisms of chemotherapeutic drugs.

Glucosamine resulting from the hydrolysis of chitosan has been reported to exert several biological activities and recently there was a tendency to synthesize glucosamine derivatives having different functional groups important for some specific activities.

The object of the present invention is to prepare quaternized amino glucosamine and to provide a composition for anticancer capable of increasing anticancer treatment effect by exerting anticancer effect via induction of apoptosis by quaternized amino glucosamine.

DISCLOSURE

Technical Problem

Such object of the present invention was accomplished by the method that glucosamine was prepared by hydrolyzing chitosan and quaternized amino glucosamine was obtained using glucosamine.

Technical Solution

The present invention provides the quaternized amino glucosamine (QAGlc) compound having anticancer effect of formula 1.

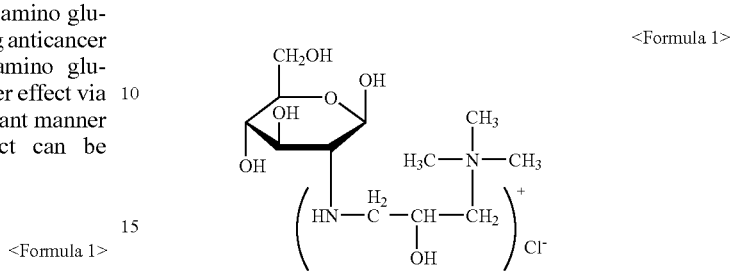

<Formula 1>

The present invention also relates to a composition for anticancer comprising the quaternized amino glucosamine of formula 1 as effective component.

The composition for anticancer can be prepared in the form of inhalation powders, tablet, capsule, powders, ointment composition, solution, gel, paste, patch and granule.

In the followings, the present invention will be illustrated with reference to examples and experimental examples. However, the present invention is not restricted by such examples.

ADVANTAGEOUS EFFECTS

The quaternized amino glucosamine of the present invention can exert an anticancer effect via induction of apoptosis in a dose and time dependant manner through which an anticancer treatment effect can be increased.

DESCRIPTION OF DRAWINGS

FIG. 1 is a graph showing FT-IR spectra of Glc and QAGlc.

FIG. 2 is a table showing cell cytotoxicity of QAGlc on various cancer cells with concentrations and time intervals dependently.

FIG. 3 is an image showing time dependant DNA damages induced by QAGlc in B16F1 cells.

FIG. 4 is an image showing concentration dependent DNA damage induced by QAGlc in B16F1 cells.

FIG. 5 is an image showing expression of p53 gene in B16F1 cells treated with QAGlc.

FIG. 6 is a graph showing induction of p53 gene expression assessed using reporter gene assay.

FIG. 7 is a graph showing induction of p21 gene expression assessed using reporter gene assay.

FIG. 8 is an Western blot analysis of phospho p53 protein expression in B16F1 cells treated with QAGlc.

BEST MODE

Example 1

Preparation of Quaternized Amino Glucosamine

As shown in reaction formula 1, glucosamine was prepared from acidic hydrolysis of chitosan by hydrolyzing chitosan with concentrated HCL for 3 h and resultant glucosamine hydrochloride was precipitated with 100% ethanol. Glucosamine hydrochloride was quaternized by reacting with 2,3-epoxypropyl chloride and tri-methyl amine.

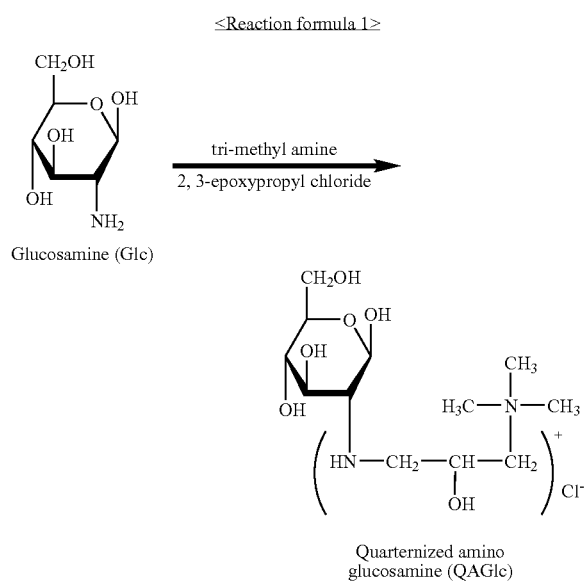

For the synthesis, pH of the trimethylamine solution was first adjusted to 2.0 to increase the boiling point. Then epoxypropyl chloride at same molar ratio was added dropwise and the pH was maintained at 9 using IM NaOH solution. Glucosamine was then added at same molar ratio and reaction was proceeded by stirring for 24 h. Throughout the reaction pH was maintained at 9.0 product was extracted using ethanol, methanol and tri hydrofluoride and quaternized amino glucosamine was obtained as a dark brown fluffy solid. Structure of newly synthesis was confirmed by elemental analyses and FT-IR. The result of elemental analysis was demonstrated in table 1 and the result of FT-IR was shown in FIG. 1. Bend absorption observed at 1480 cm.sup.-1 in QAGlc by FT-IR, clearly confirmed the quaternization of glucosamine (substitution of $N(CH_3)_3$ group).

TABLE 1

| | Carbon content (%) | | Hydrogen content (%) | | Nitrogen content (%) | |
|---|---|---|---|---|---|---|
| | Anal. | Cal. | Anal. | Cal. | Anal. | Cal. |
| Glc | 33.48 | 33.42 | 6.61 | 6.54 | 6.49 | 6.51 |
| QAGlc | 43.61 | 43.57 | 8.19 | 8.23 | 8.52 | 8.47 |

MODE FOR INVENTION

Experimental Example 1

Anticancer Effect

In order to assay the cell cytotoxicity of glucosamine and quaternized amino glucosamine on colon cancer cell (SW480), lung cancer cell (A549), mouse melanoma cell (B16F1), leukemia cancer cell (HL60) and liver cancer cell (Hep3B), MTT assay was performed with different sample concentrations and incubation time intervals.

Cells were cultured in microtiter 96-well plates with serum free media and treated with different sample concentrations for varying time intervals and anticancer effect was assessed using MTT cell viability assay. The result was represented in FIG. 2. QAGlc exerted a clear anticancer effect after 36 h of treatment. Moreover, the effect was concentration dependent.

Experimental Example 2

Detection of Apoptosis by DNA Fragmentation Assay

In order to examine anticancer effect and mechanism of QAGlc, B16F1 cells cultured in 10 cm culture dishes were pre-treated with different concentrations of QAGlc and apoptosis was induced with 2 mM $H_2O_2$. Then, cell incubation was performed for different time periods. Cell was rinsed and total DNA was extracted with the standard procedure. DNA was electrophoresed on a 2% agarose gel and DNA fraction was visualized using ethedium bromide staining. The result was represented in FIG. 3.

DNA damage was first observed after 36 h with 100 μg/ml concentration. Prolongation of incubation (after 36 h) exerted a clear effect DNA damage by all the tested concentrations dose-dependently.

B16F1 cells cultured in 10 cm culture dishes were pre-treated with different concentrations of QAGlc and apoptosis was induced with 2 mM $H_2O_2$. After incubating for 48 h, genomic DNA was extracted and electrophoresed on a 2% agarose gel. The result was represented in FIG. 4.

QAGlc exerted a higher DNA damage dose-dependently, which shows induction of apoptosis. At a concentration of 100 μg/ml, QAGlc exerted a higher DNA damage which means instructed.

Experimental Example 3

Reverse Transcription-Polymerase Chain Reaction (RT-PCR)

B16F1 cells were treated with QAGlc and total RNA was extracted. PCR was carried out using RT-generated cDNA encoding p53, p21 and GSPDH with their specific primers to amplify p53 and G3PDH mRNA. PCR products were analyzed on a 2% agarose gel. The mRNA of G3PDH served as an internal control for sample loading and mRNA integrity. The result was represented in FIG. 5.

After 24 h and 36 h of incubation, p53 transcription was up-regulated by QAGlc. This effect was much higher than that of etoposide, a well-known anticancer compound.

Experimental Example 4

Transfection and Gene Reporter Assay

B16F1 cells were transfected with p53-luc, p21-Luc reporter vectors and β-galactosidase expression vector by lipofectamine (Invitrogen) transfection method. After 24 h of transfection, cells were subcultured into 24 well plates and cells treated with different concentrations of QAGlc. The luciferase activity value was normalized to transfection efficiency monitored by the cotransfected β-galactosidase expression vector. The level of induction of luciferase was determined as a ratio in comparison to cells with no stimulation. The result was represented in FIG. 6.

p53 gene expression was up-regulated dose dependently by QAGlc and at 100 μg/ml the effect was 2-fold than that of etaposide.

According to the method described above, p21 gene was transfected to B16F1 cells according to the method described above and gene expression after the treatment of QAGlc was determined by relative luciferase activity. The result was represented in FIG. 7.

All the concentrations of QAGlc significantly enhanced p21 gene expression compared to the control.

Experimental Example 5

Western Blot Analysis

After treatment of QAGlc for different time intervals, cells were lysed in RIPA buffer [10 mmol Tris-HCL (pH 7.4), 1% deoxycholate, 1% NP40, 150 mmol NaCl, 0.1% SDS, 0.2 mmol phenylmethyl sulfonyl fluoride, 1 mg/L aprotinin and 1 mg/L leupeptin] for 30 min on ice. The lysates were centrifuged at 12,000×g for 15 min to remove debris. Protein samples were resolved using a 420% Novex gradient gel (Invitrogen, USA), electrotransferred onto a nitrocellulose membrane, and blocked with 10% skim milk. Monoclonal antibodies of phosphorylated p-53 (Cat. No, Chemicon, CA, USA) were used to detect phosphor-p53 protein using chemiluminescent ECL assay kit (Amersham Pharmacia Biosciences, NJ, USA) according to the manufacturer's instructions. Western blot bands were quantified using ImageMaster software (Amersham Pharmacia Biosciences, NJ, USA). The result was represented in FIG. 8.

As shown in FIG. 8, the results clearly exhibited that treatment of QAGlc increase phospho p53 protein level in a time dependant manner indicative of up-regulation of p53 gene expression.

Glucosamine prepared from acidic hydrolysis of chitosan was quaternized by reacting with 2,3-epoxypropyl chloride and tri-methyl amine. FT-IR data clearly confirmed the quaternization of glucosamine with a bend absorption of $N(CH_3)_3$ at 1480 cm$^{-1}$.

We could provide evidence that quaternized amino glucosamine exerts an anticancer effect on murinemelanoma cells (B16F1) via induction of apoptosis in a dose and time dependant manner.

B16F1 cells were treated with different concentrations of quaternized amino glucosamine and cytotoxicity was determined using MTT assay. A clear anticancer effect was observed after 48 h of incubation with concentrations below 0.01%. Apoptosis was confirmed by agarose gel electrophoresis of DNA fragmentation and FACS analysis clearly demonstrated that quaternized amino glucosamine increase the production of apoptotic cells. RT-PCR products exhibited that QAGlc induce apoptosis via induction of p53 and p21 genes in time dependant manner. This effect could be confirmed when the B16F1 cells were transfected with promoter plasmids of p53 and p21 treated with different concentrations of QAGlc. Induction of phosphor p53 observed in western blot analysis further confirmed that quaternized amino glucosamine induce apoptosis via p53 dependant pathway.

INDUSTRIAL APPLICABILITY

The quaternized amino glucosamine of the present invention exerts an anticancer effect via induction of apoptosis in a dose and time dependant manner through which an anticancer treatment effect can be increased such that the present invention is medical pharmaceutically useful invention.

The invention claimed is:

1. A quaternized amino glucosamine of formula 1:

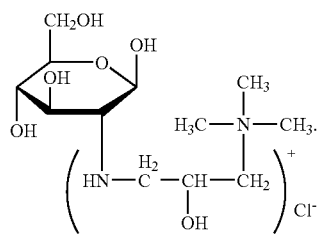

<Formula 1>

2. A composition for anticancer comprising the quaternized amino glucosamine of claim 1 as effective component in an amount of 1-100 μg/ml.

3. The composition for anticancer according to claim 2 which is prepared in the form of dispersant, tablet, capsule, powders, ointment composition, solution, gel, paste, patch and granule.

* * * * *